United States Patent
Clark et al.

(10) Patent No.: US 10,557,823 B2
(45) Date of Patent: Feb. 11, 2020

(54) ION FILTER FOR MASS SPECTROMETER

(71) Applicant: Smiths Detection-Watford Limited, Hertfordshire (GB)

(72) Inventors: Alastair Clark, Hertfordshire (GB); Jonathan Atkinson, Hertfordshire (GB)

(73) Assignee: SMITHS DETECTION-WATFORD LIMITED, Hertfordshire (GB)

( * ) Notice: Subject to any disclaimer, the term of this patent is extended or adjusted under 35 U.S.C. 154(b) by 0 days.

(21) Appl. No.: 15/518,574

(22) PCT Filed: Oct. 14, 2015

(86) PCT No.: PCT/GB2015/053032
§ 371 (c)(1),
(2) Date: Jul. 17, 2017

(87) PCT Pub. No.: WO2016/059406
PCT Pub. Date: Apr. 21, 2016

(65) Prior Publication Data
US 2017/0241951 A1 Aug. 24, 2017

(30) Foreign Application Priority Data
Oct. 14, 2014 (GB) .................................. 1418199.4

(51) Int. Cl.
*G01N 27/62* (2006.01)
*H01J 49/00* (2006.01)
*H01J 49/42* (2006.01)

(52) U.S. Cl.
CPC .......... *G01N 27/622* (2013.01); *H01J 49/004* (2013.01); *H01J 49/005* (2013.01); *H01J 49/0045* (2013.01); *H01J 49/421* (2013.01)

(58) Field of Classification Search
CPC ... G01N 27/622; G01N 27/624; H01J 49/005; H01J 49/421; H01J 49/004; H01J 49/0045
See application file for complete search history.

(56) References Cited

U.S. PATENT DOCUMENTS 6,348,688 B1 * 2/2002 Vestal ..................... H01J 9/004
250/282
7,265,345 B2 * 9/2007 Hashimoto .......... G01N 27/622
250/281

(Continued)

FOREIGN PATENT DOCUMENTS

CA      2413287 A1    1/2002
CN   101647086 A    2/2010

(Continued)

OTHER PUBLICATIONS https://en.wikipedia.org/wiki/Ion-mobility_spectrometry, Dec. 21, 2013.*

(Continued)

*Primary Examiner* — Wyatt A Stoffa
(74) *Attorney, Agent, or Firm* — Kevin E. West; Advent, LLP (57) ABSTRACT

An ion filter for a mass spectrometer, the apparatus comprising an ion modifier; an ion selector configured to select a subset of a sample of ions based on their mobility in a gas; and a controller configured to operate the ion modifier in a first mode to modify the ions selected by the ion selector to provide daughter ions, and configured to operate the ion modifier in a second mode to output the ions selected by the ion selector; wherein the ion filter is adapted for providing output ions from the ion modifier to an intake of a mass spectrometer.

13 Claims, 4 Drawing Sheets

(56) References Cited

U.S. PATENT DOCUMENTS

| | | | |
|---|---|---|---|
| 7,378,650 B2* | 5/2008 | Hashimoto | G01N 27/622 250/281 |
| 7,718,960 B2* | 5/2010 | Hashimoto | G01N 27/622 250/281 |
| 9,683,965 B2* | 6/2017 | Clemmer | G01N 27/622 |
| 2002/0014586 A1* | 2/2002 | Clemmer | G01N 27/622 250/287 |
| 2002/0070338 A1* | 6/2002 | Loboda | G01N 27/622 250/287 |
| 2002/0070339 A1* | 6/2002 | Clemmer | G01N 27/622 250/299 |
| 2003/0020012 A1* | 1/2003 | Guevremont | G01N 27/624 250/287 |
| 2004/0094702 A1 | 5/2004 | Clemmer | |
| 2006/0071159 A1* | 4/2006 | Hashimoto | G01N 27/622 250/287 |
| 2009/0283674 A1 | 11/2009 | Pesch | |
| 2010/0051800 A1 | 3/2010 | Atkinson | |
| 2010/0127164 A1* | 5/2010 | Atkinson | G01N 27/622 250/282 |
| 2010/0230588 A1* | 9/2010 | Atkinson | G01N 27/624 250/283 |
| 2011/0198493 A1* | 8/2011 | Clemmer | G01N 27/622 250/282 |
| 2012/0056085 A1 | 3/2012 | Giles et al. | |
| 2012/0228491 A1* | 9/2012 | Wu | G01N 27/622 250/282 |
| 2012/0326023 A1* | 12/2012 | Kozole | G01N 27/622 250/282 |
| 2013/0292562 A1* | 11/2013 | Clemmer | G01N 27/622 250/282 |
| 2013/0299712 A1 | 11/2013 | Atkinson | |
| 2014/0339417 A1* | 11/2014 | Hendrikse | H01J 49/0031 250/282 |
| 2015/0069229 A1 | 3/2015 | Taylor et al. | |

FOREIGN PATENT DOCUMENTS

| | | | |
|---|---|---|---|
| CN | 102449727 A | 5/2012 | |
| CN | 102768936 A | 11/2012 | |
| CN | 103460330 A | 12/2013 | |
| CN | 104126115 A | 10/2014 | |
| GB | 2421843 A | 7/2006 | |
| GB | 2457769 A | 9/2009 | |
| GB | 2515164 A | 12/2014 | |
| WO | 2006061593 A2 | 6/2006 | |
| WO | 2007054712 A2 | 5/2007 | |
| WO | 2013121287 A1 | 8/2013 | |
| WO | WO2013121287 A1 * | 8/2013 | G01N 27/622 |

OTHER PUBLICATIONS

International Search Report dated Feb. 8, 2016 for PCT/GB2015/053032.

Combined Search and Examination Report dated May 12, 2015 for Application No. GB1418199.4.

Search Report dated Jun. 22, 2017 for United Kingdom Appln. No. GB1418199.4.

Office Action for Chinese Appln No. 201580056101.3 dated Aug. 3, 2018.

Office Action for Russian Patent Application No. 2017114148/07, dated Apr. 10, 2019.

* cited by examiner

ION FILTER FOR MASS SPECTROMETER

FIELD OF INVENTION

The present invention relates to methods and apparatus for identifying substances of interest, and more particularly to methods and apparatus for selecting and/or modifying ions to assist in the identification of a substance of interest in a sample. These methods and apparatus may be useful in mass spectrometry and may employ ion mobility techniques.

BACKGROUND

There is a need to detect traces of substances of interest such as explosives, narcotics and chemical warfare agents. Reliable and accurate identification is critical. Analysis may be performed using spectrometers, such as ion mobility spectrometers and/or mass spectrometers.

Mass spectrometry works by ionizing chemical compounds to generate charged molecules or molecule fragments and measuring their mass-to-charge ratios. In a typical mass spectrometry procedure ions are separated according to their mass-to-charge ratio, typically by accelerating them and measuring the degree to which they are deflected by an applied electric or magnetic field. Some mass spectrometers operate using ion traps. Mass spectra reflect the relative abundance of detected ions as a function of their mass-to-charge ratio. The ions can be identified by comparing known masses to the identified masses or by comparing obtained spectra to known spectra. Ions of the same mass-to-charge ratio will undergo the same amount of deflection, but a single mass-charge ratio may be associated with a number of different species of ions.

Ion mobility spectrometers (IMS) can identify material from a sample of interest by ionizing the material (e.g., molecules, atoms) and measuring the time it takes the resulting ions to travel a known distance under a known electric field. This is known as time of flight ion mobility spectrometry—TOFIMS. Each ion's time of flight can be measured by a detector, and the time of flight is associated with the ion's mobility. An ion's mobility relates to its mass and geometry. Therefore, by measuring the time of flight of an ion in the detector it is possible to infer an identity for the ion. These times of flight may be displayed graphically or numerically as a plasmagram. Other kinds of ion mobility spectrometry also exist. For example, in differential ion mobility spectrometry ions are selected based on the dependency of the ion mobility on electric field strength. To do this, ions may be subjected to varying electric field strengths selected so that only ions having a selected differential mobility are able to pass though the spectrometer. For example, in field asymmetric ion mobility spectrometry ions are separated by the application of a high-voltage asymmetric waveform at radio frequency (RF) combined with a DC voltage. As the electric field varies, depending on the ratio of the high-field and low-field mobility of an ion, it will migrate toward one or the other electrode. Only ions with specific differential mobility will pass through the device.

Other ion mobility techniques use a flow of carrier gas which carry ions between electrodes. Ions can be deflected from their path in the flow of gas by an electric field applied between the electrodes across the direction of (transverse to) the flow of carrier gas. By scanning the strength of the applied field ions having different mobility can be selected.

SUMMARY OF INVENTION

Aspects and examples of the invention are set out in the appended claims.

BRIEF DESCRIPTION OF DRAWINGS

Embodiments of the disclosure will now be described by way of example only with reference to the accompanying drawings in which.

In the drawings like reference numerals are used to indicate like elements.

SPECIFIC DESCRIPTION

Embodiments of the disclosure provide an ion filter for a mass spectrometer. As illustrated in the drawings, and explained in more detail below, an ion filter may comprise an ion selector and an ion modifier. The ion selector selects a subset of a sample of ions based on their mobility in a gas. The ion modifier may be controlled to either modify ions to provide daughter ions which in turn are provided to a mass spectrometer for analysis, or to allow the subset of ions to pass unmodified to the mass spectrometer.

The ion modifier may be arranged to modify only the subset of ions selected by the ion selector, or it may be arranged to modify the sample of ions before the ion selector selects a subset of the daughter ions, for example the ion modifier may be integrated in the ion selector or arranged between a source of samples of ions and the ion selector.

Selecting based on ion mobility may comprise selecting based on differential ion mobility, and/or based on the time of flight ion mobility, for example based on ion mobility at a selected electric field, for example based on the 'low field' ion mobility in which the ion mobility is not dependent on field strength (e.g. fields of up to about 500 $Vcm^{-1}$) and/or based on any other mobility characteristic.

Embodiments of the disclosure enable a sample to be analysed to identify a substance of interest by operating the ion selector to select a first subset of ions from a sample, and allowing the first subset of ions to pass unmodified for analysis in a mass spectrometer, and then operating the ion selector to select a second subset of ions from the same sample, and then operating the ion modifier to modify this second subset of ions to output the daughter ions for analysis in the mass spectrometer. The first subset of ions and the second subset of ions may be obtained from the same sample (e.g. from a single sample of vapour). However in some embodiments they may also be obtained from separate samples obtained from the same substance of interest (e.g. from volatilising a single swab of a substance of interest).

Figure 1:
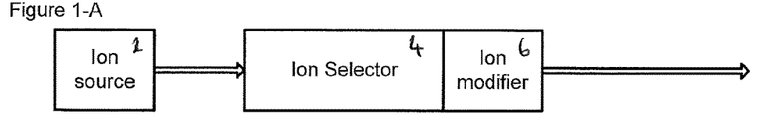
FIG. 1 shows a very schematic diagram of three possible implementations of the disclosure.

FIG. 1 illustrates three possible configurations of an ion filter for a mass spectrometer. In the first illustration, FIG. 1-A shows an ion selector 4 arranged to obtain ions from an ion source 2, and to select a subset of these ions based on their mobility in a gas. The ion selector 4 can then provide this subset of ions to an ion modifier 6 which may be operated selectively to either (a) modify the subset of ions before they are analysed by the mass spectrometer or (b) to allow the ions to pass without modification. In the second illustration FIG. 1-B shows an ion modifier 6 arranged to obtain ions from an ion source 2 and which may be operated to modify the ions before providing them to an ion selector 4 which may select a subset of these ions before they are provided to the mass spectrometer to be analysed. In the third illustration the ion selector includes an integrated ion modifier 6, in this configuration the ion selection apparatus itself includes an ion modifier 6. This ion modifier 6 can be operated to modify at least some of the ions in the ion selector 4, and the ion selector 4 can be operated to provide a subset of the ions from the ion source 2 (perhaps some of which may have been modified) for analysis in the mass spectrometer.

Figure 2:
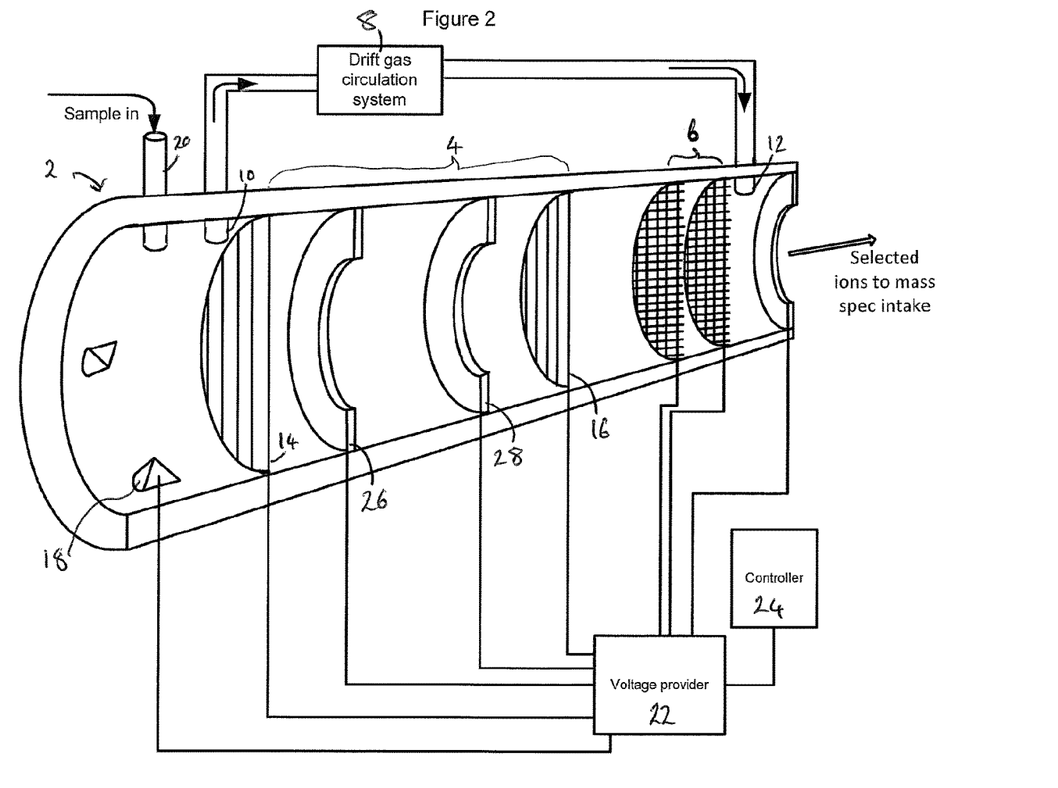
FIG. 2 shows a schematic part cut-away view of an ion filter.

FIG. 2 shows an ion filter for a mass spectrometer, the apparatus illustrated in FIG. 2 is one example of the configuration illustrated in FIG. 1-A. The apparatus illustrated in FIG. 2 comprises an ion source 2 arranged to provide ions to the ion filter. The ion filter comprises an ion selector 4 and an ion modifier 6 arranged to provide selected and/or modified ions to a mass spectrometer for analysis.

The ion source 2 may comprise an inlet 20, such as a pinhole or membrane inlet, for obtaining a sample of gaseous fluid such as a vapour or gas, and an ioniser 18 for ionising the sample. The ioniser 18 may comprise a source of ionising radiation such as a corona discharge element or a radioactive source. In some embodiments the sample may be ionised using an ionised reactant gas.

The ion selector 4 shown in FIG. 2 comprises a drift chamber separated from the ion source 2 by a first ion gate 14. The ion selector 4 may comprise a second ion gate 16, separated from the first ion gate 14 by the drift chamber. The first ion gate 14 and the second ion gate 16 may each comprise two electrodes which may each comprise a plurality of elongate conductors. The electrodes of each ion gate may be interdigitated or, in another configuration, interleaved and at least partially non-coplanar (e.g. spaced apart in a direction of travel of the ions), for example to provide an ion shutter such as a Bradbury-Nielsen gate, or a Tyndall-Powell gate.

The drift chamber may comprise a series of drift electrodes 26, 28 for applying a voltage profile along the drift chamber to move ions from the first ion gate 14 along the drift chamber toward the second ion gate 16. The ion modifier 6 may be arranged for ions to pass from the drift chamber, through the second ion gate 16 into the ion modifier 6 before being passed on to a mass spectrometer (not shown in FIG. 2).

The ion modifier 6 may comprise two electrodes which may be spaced apart from the second ion gate 16. Each of the ion modifier electrodes can comprise an array of conductors, such as a grid, for example a mesh, arranged across the direction of travel of the ions from the second ion gate 16 towards an outlet which may be coupled for providing ions to a mass spectrometer. As illustrated, the conductors of each ion modifier electrode may have gaps between them such that ions can pass through each electrode by travelling through the gaps. In one example ions pass through the gaps between the conductors of the electrode into a region between the electrodes and subsequently out of the region through the gaps between the conductors of the ion modifier 6. While the ions are in the region between the electrodes they can be subjected to a radio frequency, RF, electric field to fragment them. For example the ion modifier may be configured to subject ions to an alternating electric field which is symmetric (e.g. has a small or zero DC component). In some embodiments the ion modifier 6 may comprise a heater in addition to or as an alternative to these two electrodes. In some embodiments the ion modifier 6 may comprise more than two electrodes. In some examples of the disclosure more than one ion modifier may be used.

In the apparatus illustrated in FIG. 2, the ion selector comprises the ion modifier 6, in that example it is arranged between the first ion gate 14, and the second ion gate 16. In other examples in which the ion selector comprises the ion modifier 6 one or more ion gates of the ion selector (such as the first ion gate 14, and the second ion gate 16 illustrated in FIG. 2) may be provided by an ion modifier 6, for example by a combined ion gate and ion modifier as described below. Examples of a combined ion gate and ion modifier are provided in the applicant's co-pending European patent application published as EP2666183, the entirety of which is hereby incorporated by reference.

A voltage provider 22 may be coupled to the ioniser 18, the first ion gate 14, the second ion gate 16, the drift electrodes 26, 28, and the ion modifier 6. A controller 24 may be coupled to control operation of the voltage provider 22.

A drift gas circulation system 8 may be coupled to a drift gas outlet 10 of the ion selector 4, and to a drift gas inlet 12 of the ion modifier 6. The ion modifier 6 may be arranged so that drift gas introduced in the ion modifier 6 flows through the second ion gate 16 into the drift chamber towards the first ion gate 14. The drift gas circulation system 8 may be configured to provide a flow of drift gas in a direction generally opposite an ion's path of travel from the first ion gate 14 to the second ion gate 16. Example drift gases include, but are not limited to, nitrogen, helium, air, air that is re-circulated (e.g., air that is cleaned and/or dried). It will be appreciated in the context of the present disclosure that in the example illustrated in FIG. 2, an electric field is applied by the voltage provider (e.g. using the drift electrodes and possibly also other electrodes) to move ions against this flow of drift gas along the drift chamber towards the second ion gate 16.

The first ion gate 14 may be operable to be opened to allow ions to pass from the ion source 2 into the drift chamber, and operable to be closed to inhibit the passage of ions. Likewise, the second ion gate 16 may be operable to be opened to allow ions to pass from the drift chamber to the ion modifier, or to be closed to inhibit the passage of ions. This provides one way to select a subset of ions from a sample. Selecting a subset of ions (e.g. less than all of the ions from the sample) may comprise allowing some ions from a sample to pass the first ion gate 14, and then inhibiting the passage of some of these ions through the second ion gate 16, for example by closing the second ion gate 16. Accordingly, the controller 24 may select a subset of a sample of ions based on their mobility in the drift gas by controlling the relative timing of opening the first ion gate 14 and the second ion gate 16. For example the timing of opening the second ion gate 16 may be selected based on the timing of opening the first ion gate 14 to allow only those ions having a selected time of flight along the drift chamber (and/or a selected range or ranges of times of flight) to pass from the ion selector 4 to the ion modifier.

The ion modifier 6 may be operable in a first mode to apply energy to ions to modify them, for example by raising their effective temperature, for example by subjecting the ions to an RF electric field. The energy applied to the ions in this first mode of operation may be selected based on the amount of energy required to fragment selected ions, for example ions of a target substance, and adduct ions formed between that target substance and a known reactant that is present in the ion source 2 or the ion selector 4. Target substances include narcotics, explosives, chemical warfare agents and other contraband. The energy applied may be selected by controlling the amplitude and/or frequency of the electric field applied by the ion modifier. In some embodiments the energy may be thermal energy and the amount of energy applied may be controlled by controlling temperature, for example using a heater. The ion modifier may also be operable in a second mode to allow ions to pass from the ion selector 4 to the mass spectrometer without subjecting the ions to energy to modify them. For example, in this second mode the ion modifier may be operated to apply less energy to the ions than is applied in the first mode, for example it may be switched off.

In operation, the ioniser 18 is operated to provide a sample of ions from a substance of interest. The controller 24 may then open the first ion gate 14 to allow some ions from the sample to travel along the drift chamber against the flow of drift gas. The time of arrival of the ions at the second ion gate 16 is determined by their mobility through the gas and the electric field applied along the drift chamber by the drift electrodes 26, 28. The controller 24 then controls the second ion gate 16 to inhibit the passage of some of the ions and to allow others to pass. For example, ions which arrive at the second ion gate 16 in a selected time window (or a series of time windows) after the opening of the first ion gate 14 may be allowed to pass through the second ion gate 16 while ions arriving outside of this window (or windows) may be inhibited from passing for example by being stopped or deflected by the ion gate. Accordingly, only a selected subset of ions from the ion source 2 may be passed through the ion selector 4 to the ion modifier.

The controller 24 can then operate the ion modifier 6 in either (a) the first mode to modify this selected subset of ions and to provide the daughter ions obtained by this modification process to the mass spectrometer, or (b) the second mode to allow the selected subset of ions to pass through to the mass spectrometer without modifying them. For example, the controller 24 may first select a subset of ions from a sample to be passed to the mass spectrometer, and operate the ion modifier in the second mode to provide the (unmodified) subset of ions to the mass spectrometer. The controller 24 may then subsequently provide a second subset of ions to the ion modifier and operate the ion modifier in the first mode so that daughter ions can be provided to the mass spectrometer. The subset of ions provided without modification, and the daughter ions obtained by modifying a subset of ions may be a comparable subset (e.g. a subset from the same sample and/or having the same mobility/mobilities). Both subsets may then be analysed in the mass spectrometer to identify the substance of interest.

The order of operation explained above may also be reversed so that the daughter ions are provided to the mass spectrometer first, and the parent ions are provided subsequently. The first and second subset of ions may be from the same sample, and may be selected to have the same mobility/mobilities, e.g. by using the same time window(s) for opening and closing the ion gates.

In some embodiments, the controller 24 may control the timing of operation of the ion modifier 6 in the first mode so that only some (e.g. less than all) of the selected subset of ions are modified. For example where the selected subset of ions passes through the ion modifier during a particular time window (or windows) e.g. as determined by their mobility, the controller 24 may operate the ion modifier to modify ions during a selected interval during this time window.

As mentioned briefly above, in some embodiments the first ion gate 14 or the second ion gate 16 may be provided by one or more electrodes of the ion modifier 6. For example, the controller 24 may be configured to apply a voltage to the ion modifier 6 to inhibit the passage of ions through the ion modifier and/or to deflect ions travelling along the drift chamber so that the ion modifier performs the function of the second ion gate. For example, the controller may be configured to operate a first electrode of the ion modifier 6 as an ion gate. For example, one electrode of the ion modifier 6 may comprise a plurality of conductors arranged to be operated as an ion gate, for example an ion shutter such as a Bradbury-Nielsen gate, or a Tyndall-Powell gate. Any of the ion gates of any of the embodiments described herein may be provided by an ion modifier arranged in this way. Examples of combined ion gates and ion modifiers are provided in the applicant's co-pending European patent application published as EP2666183, the entirety of which is hereby incorporated by reference. In some embodiments the apparatus comprises more than one ion modifier 6.

In some examples the apparatus of FIG. 2 only comprises a single ion gate, and that ion gate may be provided by a combined ion gate and ion modifier, for example provided by one or more electrodes of the ion modifier 6.

In the example illustrated in FIG. 2, the drift gas circulation system 8 is arranged to provide a flow of drift gas through both the ion selector 4 and the ion modifier 6, for example, in the configuration shown in FIG. 2 the ion selector 4 and ion modifier 6 may be at the same gas pressure. In some examples however, ions may be passed from the ion selector 4 (e.g. from the second ion gate 16) to the ion modifier through a narrow passage arranged to permit a gas pressure difference to be maintained between the two.

Figure 3:
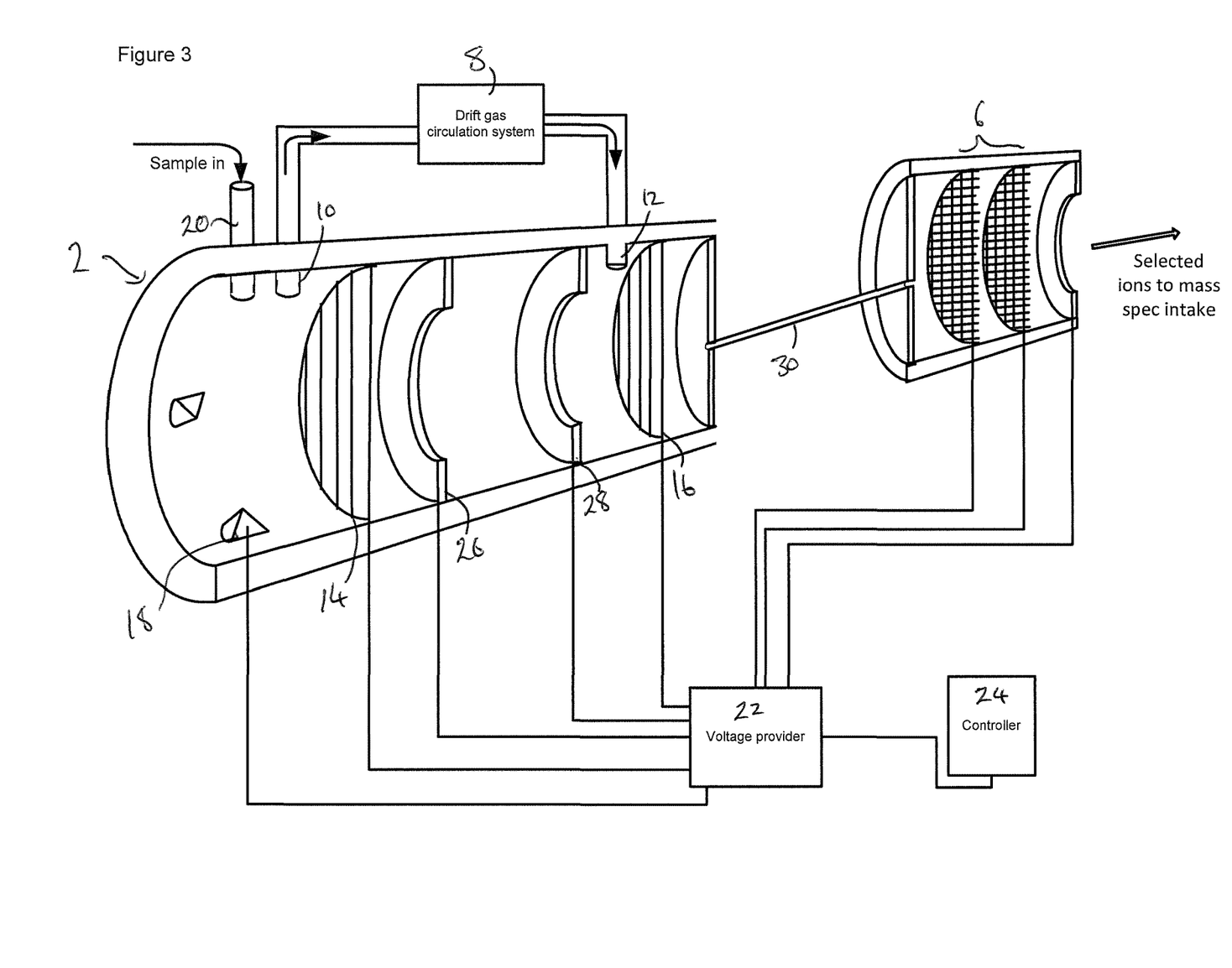
FIG. 3 shows a schematic part cut-away view of another ion filter.

FIG. 3 illustrates a configuration similar to that shown in FIG. 2, but in the example shown in FIG. 3 the ion modifier and the ion selector may be arranged in separate chambers. By pumping on one or both of the two chambers the pressure in each chamber may be controlled separately, for example a pressure difference may be maintained between them. As illustrated, in these embodiments, the use of a narrow passage, such as a capillary 30, allows ions to travel between the ion selector and the ion modifier 6. Ion focusing apparatus such as an ion guide may be arranged to direct ions along this narrow passage. In this configuration the pressure in the ion selector and/or the ion modifier 6 may be at least 500 millibar, for example at least 800 millibar, for example about atmospheric pressure. The gas pressure in the ion modifier 6 may be different from, e.g. lower than, the pressure in the ion selector.

It will be appreciated that the configuration shown in FIG. 3 may be reversed so that the ion modifier 6 is arranged between the ion source 2 and the ion selector, for example the ion source 2 may be arranged to provide ions to the ion modifier 6, and the controller 24 can select whether or not to operate the ion modifier 6 to modify these ions before they are passed to the ion selector. In this configuration the ion modifier 6 and the ion source 2 may be arranged in separate chambers (which may be at different pressures), and as described with reference to FIG. 3 ions may be passed from the ion modifier 6 to the ion selector along a narrow passage such as a capillary 30. In this configuration the ion selector may be operated to select a subset of daughter ions produced by the ion modifier 6, and the ion modifier 6 can be operated in either the first mode to modify ions or in the second mode to allow unmodified ions to pass to the ion selector.

Figure 4:
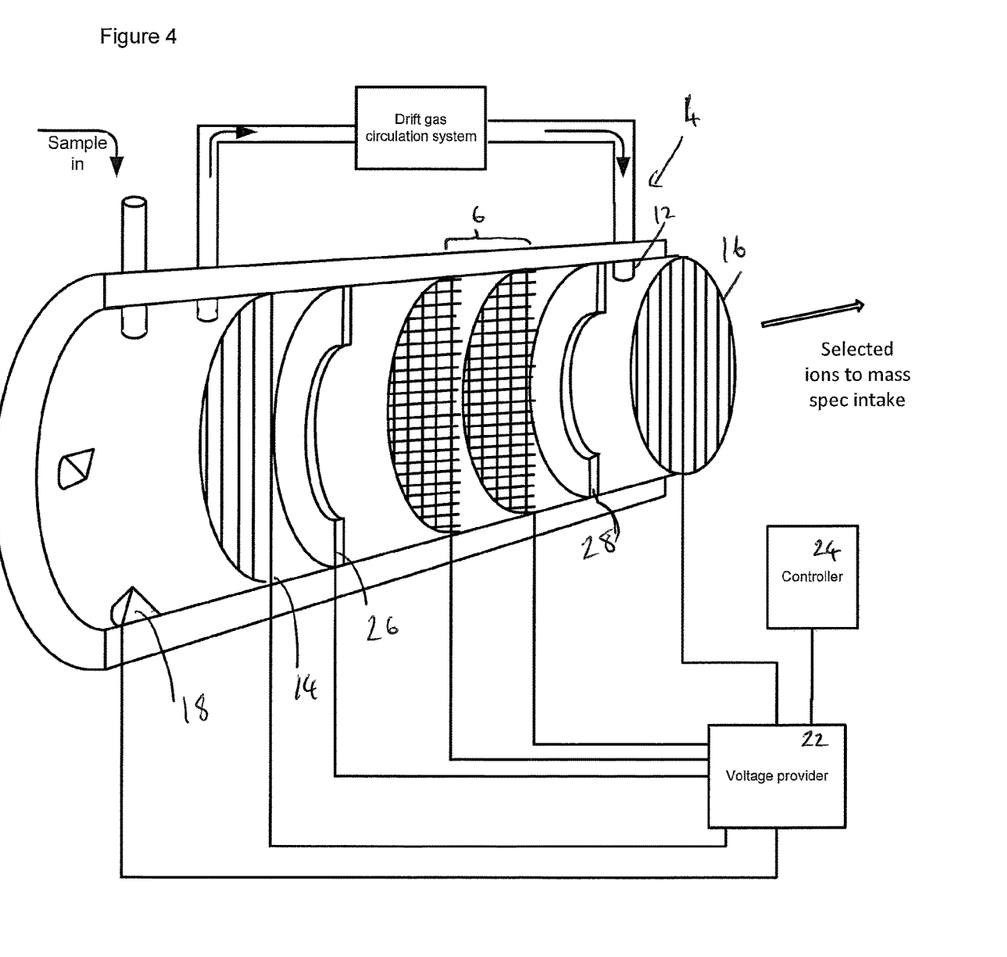
FIG. 4 shows a schematic part cut-away view of another ion filter.

FIG. 4 illustrates another example similar to that shown in FIG. 2. In FIG. 4, as in FIGS. 2 and 3 the ion selector is based on a time of flight ion mobility spectrometry method—for example wherein the controller 24 is configured to select the subset of ions by controlling the timing of operating the second ion gate 16. In the apparatus illustrated in FIG. 4, the second ion gate 16 is arranged between the ion modifier 6 and the output to the mass spectrometer, for example the ion modifier 6 may be arranged in the drift chamber between the first ion gate 14 and the second ion gate 16 of the ion selector. As illustrated in FIG. 4, the ion modifier 6 may be arranged to modify ions in a region in the drift chamber of the ion selector, for example the ion modifier 6 may comprise two electrodes as described above with reference to FIG. 2, and these may be arranged to subject ions in this region to electric fields (e.g. RF electric fields) which are stronger than the electric fields used to move ions along the drift chamber. The ion modifier 6 electrodes may be arranged to subject the ions to an electric field aligned with the direction of travel of the ions along the drift chamber. The alignment of the electric field from the ion modifier 6 with the direction of travel of the ions is unlikely to be perfect or uniform. For example the direction of the electric field will depend on the geometry and relative arrangement of the conductors which make up the ion modifier electrodes.

Figure 5:
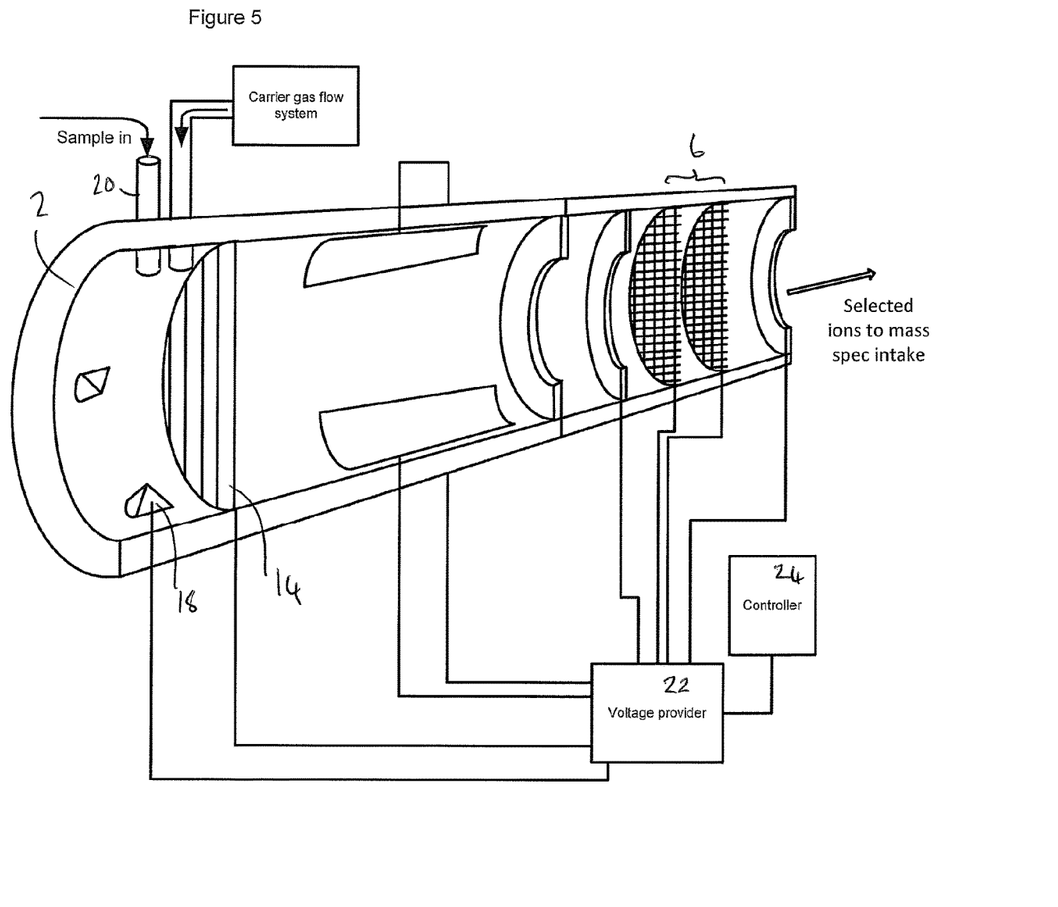
FIG. 5 shows a schematic part cut-away view of another ion filter.

FIG. 5 illustrates an ion filter for a mass spectrometer in which an ion selector is configured to select a subset of ions based on a differential mobility technique such as a differential mobility analysis.

The apparatus of FIG. 5 may comprise an ion source 2 having the features of the ion source 2 described above with reference to FIG. 2.

The ion selector shown in FIG. 5 comprises a gas flow chamber separated from the ion source 2 by a first ion gate 14. The gas flow chamber may be arranged to allow ions to be carried by a flow of gas from the ion source 2 towards an outlet of the gas flow chamber. A carrier gas flow system may be arranged to provide the flow of carrier gas along the gas flow chamber from the ion gate 14 to the outlet. Two deflecting electrodes are arranged for applying an electric field in the gas flow chamber across the direction of (e.g. transverse to) the flow of gas.

A voltage provider 22 may be coupled to the ioniser 18, the ion gate 14, and the ion modifier electrodes also as described above with reference to FIG. 2. The voltage provider 22 may also be coupled to the deflection electrodes for applying a selected electric field perpendicular to the direction of the flow of gas.

A controller 24 is coupled to control the voltage provider 22 for operating at least one of the ioniser 18, the ion gate 14, the deflection electrodes, and the ion modifier 6. The controller 24 may be configured to control the electric field applied by the deflection electrodes so that only ions having a selected mobility characteristic, for example a selected differential mobility, are able to pass from the ion selector to be provided to the mass spectrometer for analysis.

As illustrated in FIG. 5, the outlet of the ion selector is arranged so that ions which leave the ion selector can be passed to the ion modifier 6. The ion modifier 6 may comprise two electrodes and have the features described above with reference to the ion modifier 6 illustrated in FIG. 2, the ion modifier 6 of this embodiment may also be arranged in a separate chamber as described above with reference to FIG. 3, or arranged to modify ions before (or during) their separation by the ion selector as described above with reference to FIG. 4. In operation, ions are provided from the ion source 2 into the flow of carrier gas. The flow of gas carries the ions towards the outlet of the ion selector. The voltage provider 22 applies a voltage across the deflection electrodes, to provide an electric field transverse to (e.g. perpendicular to) the direction of the flow of gas. The controller 24 selects the applied voltage to control this electric field, and this in turn selects the mobility of ions which are able to pass through the outlet of the ion selector. The controller 24 can then operate the ion modifier 6 in one of the first mode and second mode described above to modify the selected subset of ions, or to allow them to pass unmodified to the mass spectrometer. In the embodiment of FIG. 5, the ion gate 14 is optional.

The methods of operation described above with reference to FIGS. 1 to 4 may also be applied to the apparatus described with reference to FIG. 5.

It will be understood that the embodiments described are to be understood as illustrative examples. Further embodiments are envisaged. For example a field asymmetric ion mobility spectrometry technique may be used to provide the ion selector. These embodiments may reflect the configuration illustrated in FIG. 5 and the voltage provider 22 may be configured to apply an asymmetric alternating voltage, for example an RF voltage, as will be appreciated by the skilled addressee in the context of the present disclosure this may enable a subset of ions to be selected based on the electric field dependence of their mobility, for example based on their differential mobility. In some embodiments of the apparatus illustrated in FIG. 5 in addition to, or as an alternative to the use of a carrier gas a voltage may be used to move ions towards the outlet, for example electrodes similar to the drift electrodes 26, 28 illustrated in FIG. 2 may be used.

It will also be appreciated that any of the apparatus embodiments described herein may be used in methods of identifying a substance of interest. For example they may be coupled to mass spectrometers to enable mass spectrometry data (and perhaps also mobility data) associated with both modified and unmodified ions to be used in identifying the substance of interest—for example to assign one or more candidate identities to the substance. One example of such a method comprises ionising a sample of a substance.

A subset of these ions can then be selected, for example using any one of the ion selectors described herein. This first subset of sample ions may be selected to have a particular mobility characteristic, such as a particular ion mobility, for example a particular differential mobility. This first subset of sample ions may then be provided to a mass spectrometer to obtain first mass spectrometry data, for example describing the mass to charge ratios of that subset of ions.

A second subset of ions from the sample may then be obtained (for example by selecting them based on the same mobility characteristic, for example to have the same mobility characteristic(s) as the first subset of ions) of the sample ions.

This second subset of ions may then be modified, for example by fragmenting the ions for example by subjecting them to an alternating electric field. The daughter ions produced by this modification process can then also be provided to the mass spectrometer to obtain second mass spectrometry data.

The first mass spectrometry data and the second mass spectrometry data may then be used in identifying the substance of interest. It will of course be appreciated that the order in which these steps are performed may be reversed.

In addition, the mobility characteristic of at least one of the first subset of ions and the second subset of ions may also be used in identifying the substance of interest. Identifying the substance of interest may comprise assigning one or more candidate identities to the substance.

It is to be understood that any feature described in relation to any one embodiment may be used alone, or in combination with other features described, and may also be used in combination with one or more features of any other of the embodiments, or any combination of any other of the embodiments. Furthermore, equivalents and modifications not described above may also be employed without departing from the scope of the invention, which is defined in the accompanying claims.

For example, the following methods of the disclosure may also be combined with any other method described herein, and/or implemented using any of the apparatus described herein. A first such example comprises introducing a sample of vapour into a low pressure region of a spectrometry apparatus, ionising the sample, modifying the ions obtained by ionising the sample, and providing the modified ions to a detector for analysis. The gas pressure in the low pressure region may be lower than ambient pressure by at least 200 mb, for example lower than ambient pressure by at least 300 mb. Such methods may comprise moving the ions away from an ionisation region towards the detector and subjecting the ions to a radio frequency, RF, electric field having a component (for example a dominant component) aligned with the direction of movement of the ions towards the detector. The RF electric field may be applied to the ions by two electrodes spaced apart in the direction of movement of the ions towards the detector.

Some examples of the disclosure may be used to provide sample intake stage apparatus for spectrometers such as mass spectrometers. These intake stages may comprise a low pressure region having a pressure lower than 200 mb less than ambient pressure, the low pressure region may comprise an inlet 20 for obtaining a sample of gaseous fluid, an ioniser 18 for obtaining parent ions from the sample, and an ion modifier 6 configured to modify the parent ions in the low pressure region to provide daughter ions, and an outlet arranged for providing the daughter ions to the spectrometer for analysis. The ion modifier 6 may be arranged to subject the ions to an alternating radio frequency, RF, electric field aligned with, for example predominantly aligned with, the direction of movement of the ions towards the outlet.

With reference to the drawings in general, it will be appreciated that schematic functional block diagrams are used to indicate functionality of systems and apparatus described herein. It will be appreciated however that the functionality need not be divided in this way, and should not be taken to imply any particular structure of hardware other than that described and claimed below. The function of one or more of the elements shown in the drawings may be further subdivided, and/or distributed throughout apparatus of the disclosure. In some embodiments the function of one or more elements shown in the drawings may be integrated into a single functional unit. Some types of ion mobility spectrometry have been described for providing the ion selector functions of the apparatus described herein but it will be appreciated that any ion mobility based technique may be used, for example other ion mobility techniques such as travelling wave IMS techniques. Other examples and variations will be apparent to the skilled addressee in the context of the present disclosure.

For example, drift gases need not be used, some examples of the disclosure may be used in systems where the mean free path of ions is comparable to, for example greater than or equal to, the length of the drift chamber. Rather than mobility, these examples of the disclosure may measure the mass to charge ratio of the ions for example based on a time of flight measurement or based on subjecting ions to a magnetic field to deflect them from their direction of travel.

In some examples, one or more memory elements can store data and/or program instructions used to implement the operations described herein. Embodiments of the disclosure provide tangible, non-transitory storage media comprising program instructions operable to program a processor to perform any one or more of the methods described and/or claimed herein and/or to provide data processing apparatus as described and/or claimed herein.

The uses and operations of the apparatus described herein are intended also as a disclosure of the method, and the particular structure of the apparatus may not be relevant—therefore features of apparatus embodiments may be combined with the method embodiments described and claimed herein. Likewise, the methods described herein may be implemented by suitable configuration of the apparatus disclosed herein. Where appropriate, the activities and apparatus outlined herein may be implemented using controllers and/or processors which may be provided by fixed logic such as assemblies of logic gates or programmable logic such as software and/or computer program instructions executed by a processor. Other kinds of programmable logic include programmable processors, programmable digital logic (e.g., a field programmable gate array (FPGA), an erasable programmable read only memory (EPROM), an electrically erasable programmable read only memory (EEPROM)), an application specific integrated circuit, ASIC, or any other kind of digital logic, software, code, electronic instructions, flash memory, optical disks, CD-ROMs, DVD ROMs, magnetic or optical cards, other types of machine-readable mediums suitable for storing electronic instructions, or any suitable combination thereof.

Where reference is made to electrodes it will be appreciated that any arrangement of conductors may be used, for example electrodes may comprise metals or other conductors and may be at least partially exposed and/or partially insulated. The voltage providers described herein may comprise an AC power supply, which may comprise one or more step-up or step down transformers, the voltage providers may also comprise DC power supplies such as batteries or fuel cells or capacitive power stores. Combinations of AC and DC power may be used and the voltage provider may comprise an inverter for providing an AC voltage based on a DC power supply. In some embodiments the voltage provider may comprise rectifiers for providing DC voltage based on an AC power supply. Any combination of AC and DC power supply and voltage providing components may be used. In some embodiments the voltage provider may also operate as a current source.

The invention claimed is:

1. An ion filter apparatus for a mass spectrometer, the apparatus comprising:
    an ion modifier comprised of at least one of a heater or at least two electrodes;
    an ion selector comprising at least two ion gates and configured to select a subset of ions from a sample of ions based on their mobility in a gas; and
    a controller configured to operate the ion modifier in a first mode to modify the ions selected by the ion selector to provide daughter ions, and configured to operate the ion modifier in a second mode to output the subset of ions selected by the ion selector;

wherein the ion filter further includes an outlet, the outlet adapted for providing output of the at least one of the subset of ions or the daughter ions to an intake of a mass spectrometer, wherein the at least two ion gates are separated from the outlet by the ion modifier, and wherein at least one of:
the ion modifier is arranged to modify ions in a region having a gas pressure of at least 500 millibar; or
the ion selector is arranged to select ions based on their mobility in a gas having a gas pressure of at least 500 millibar.

2. The apparatus of claim 1, wherein the ion selector comprises the ion modifier.

3. The apparatus of claim 1, wherein the controller is further configured to:
operate the ion selector to select a first subset of ions from the sample of ions,
operate the ion modifier in the second mode to output the first subset of ions;
operate the ion selector to select a second subset of ions from the sample of ions, and
operate the ion modifier in the first mode to output daughter ions of the second subset of ions.

4. The apparatus of claim 3, wherein the ion selector is configured to select the first subset of ions and the second subset of ions so that, prior to operation of the ion modifier, the first subset of ions and the second subset of ions have the same mobility.

5. The apparatus of claim 1, wherein selecting ions based on mobility in a gas comprises selecting ions based on one of differential ion mobility or ion mobility.

6. The apparatus of claim 1, wherein the ion selector comprises a first electric field applier configured to move ions through a drift gas towards an ion gate, the first electric field applier comprising at least one first field-applier electrode.

7. The apparatus of claim 6, wherein the controller is configured to select the subset of ions by controlling the timing of operating the ion gate.

8. The apparatus of claim 6, wherein the ion modifier comprises a second electric field applier configured to subject ions to an alternating electric field aligned with a direction of travel of the ions through the ion modifier, the second electric field applier comprising at least one second field-applier electrode.

9. The apparatus of claim 1, wherein the ion selector is arranged to apply a deflecting electric field to deflect ions carried in a flow of gas, and the controller is configured to control the deflecting field to select the subset of ions.

10. The apparatus of claim 9, wherein the ion selector comprises one of a scannable ion filter, a differential ion mobility spectrometer, or a field asymmetric ion mobility spectrometer.

11. The apparatus of claim 1, wherein the ion modifier is adapted to apply an alternating electric field having a frequency of at least 2.5 MHz to fragment ions.

12. The apparatus of claim 2, wherein the controller is further configured to:
operate the ion selector to select a first subset of ions from the sample of ions,
operate the ion modifier in the second mode to output the first subset of ions;
operate the ion selector to select a second subset of ions from the sample of ions, and
operate the ion modifier in the first mode to output daughter ions of the second subset of ions.

13. The apparatus of claim 1, wherein the ion modifier comprises two electrodes, the electrodes comprising conductors arranged across the direction of travel of ions.

* * * * *